United States Patent [19]
Schneider et al.

[11] 4,315,938
[45] Feb. 16, 1982

[54] 4-PHENYL-4,5,6,7-TETRAHYDRO-PYRROLO [2,3-C] PYRIDINES AND SALTS THEREOF

[75] Inventors: Claus Schneider, Ingelheim am Rhein; Karl-Heinz Weber, Gau-Algesheim; Gerhard Walther, Bingen; Karin Böke, Ingelheim am Rhein; Wolf D. Bechtel, Appenheim, all of Fed. Rep. of Germany

[73] Assignee: Boehringer Ingelheim Gmbh, Ingelheim am Rhein, Fed. Rep. of Germany

[21] Appl. No.: 163,969

[22] Filed: Jun. 30, 1980

[30] Foreign Application Priority Data

Jul. 6, 1979 [DE] Fed. Rep. of Germany ....... 2927294

[51] Int. Cl.³ .................. A61K 31/44; A61K 31/445; C07D 471/04
[52] U.S. Cl. .................................... 424/267; 546/113; 546/208; 544/127; 544/141; 260/244.4; 260/326.47; 260/326.62; 260/326.5 L; 424/248.4; 424/248.57; 424/256; 260/326.5 G; 260/245.7
[58] Field of Search ......................... 546/113; 544/127; 260/244.4; 424/248.4, 248.57, 256, 267

[56] References Cited
U.S. PATENT DOCUMENTS
3,992,544  11/1976  Archibald et al. .................. 546/113

OTHER PUBLICATIONS
Nagai et al., Chem. Abst., 1978, vol. 88, No. 22555d.

Primary Examiner—John M. Ford
Assistant Examiner—Natalia Harkaway
Attorney, Agent, or Firm—Hammond & Littell, Weissenberger & Muserlian

[57] ABSTRACT

Compounds of the formula

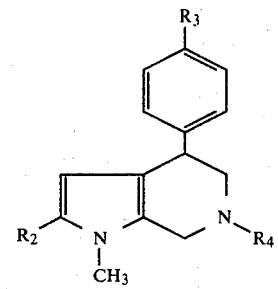

wherein
$R_2$ is hydrogen, chlorine, bromine, formyl, acetyl, alkyl of 1 to 4 carbon atoms, nitro, cyano or —CH$_2$—A;
where
A is (alkyl of 1 to 2 carbon atoms)-amino; di(alkyl of 1 to 2 carbon atoms)-amino, where one of the alkyl moieties may have a terminal hydroxyl substituent attached thereto; or a 5-, 6- or 7-membered saturated, nitrogen-containing heterocycle which is attached to the methylene group through the nitrogen atom and may have a hydroxyl or hydroxymethyl substituent attached to a ring carbon atom, and the 6-membered heterocycle may contain oxygen as an additional ring heteroatom in the p-position;
$R_3$ is hydrogen, fluorine, chlorine, bromine, methyl or methoxy; and
$R_4$ is hydrogen or alkyl of 1 to 3 carbon atoms;

and non-toxic, pharmacologically acceptable acid addition salts thereof. The compounds as well as their salts are useful as antidepressants.

10 Claims, No Drawings

4-PHENYL-4,5,6,7-TETRAHYDRO-PYRROLO [2,3-C] PYRIDINES AND SALTS THEREOF

This invention relates to novel 4-phenyl-4,5,6,7-tetrahydro-pyrrolo [2,3-c] pyridines and non-toxic acid addition salts thereof, to methods of preparing these compounds, to pharmaceutical compositions containing them as active ingredients, and to methods of using them as antidepressants.

More particularly, the present invention relates to a novel class of compounds represented by the formula

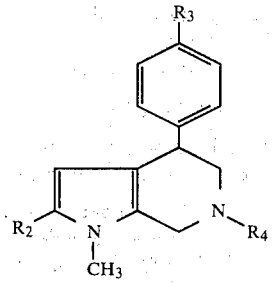

(I)

wherein
 $R_2$ is hydrogen, chlorine, bromine, formyl, acetyl, alkyl of 1 to 4 carbon atoms, nitro, cyano or —CH$_2$—A;
where
 A is (alkyl of 1 to 2 carbon atoms)-amino; di(alkyl of 1 to 2 carbon atoms)-amino, where one of the alkyl moieties may have a terminal hydroxyl substituent attached thereto; or a 5-, 6- or 7-membered saturated, nitrogen-containing heterocycle which is attached to the methylene group through the nitrogen atom and may have a hydroxyl or hydroxymethyl substituent attached to a ring carbon atom, and the 6-membered heterocycle may contain oxygen as an additional ring heteroatom in the p-position;
 $R_3$ is hydrogen, fluorine, chlorine, bromine, methyl or methoxy; and
 $R_4$ is hydrogen or alkyl of 1 to 3 carbon atoms;
and non-toxic, pharmacologically acceptable acid addition salts thereof.

A preferred subgenus thereunder is constituted by compounds of the formula I,
wherein
 $R_2$ is hydrogen, chlorine, bromine, fluorine, formyl, acetyl, methyl, nitro, cyano or —CH$_2$—A,
where
 A is dimethylamino, N-(β-hydroxyethyl)-ethylamino, morpholino, piperidino, hydroxypiperidino, hydroxymethylpiperidino, hexamethyleneimino or pyrrolidino;
 $R_3$ is hydrogen, fluorine, chlorine, bromine, or methyl; and
 $R_4$ is hydrogen, methyl or ethyl;
and non-toxic, pharmacologically acceptable acid addition salts thereof.

The compounds embraced by formula I may be prepared by the following methods:
Method A
 By cyclizing a compound of the formula

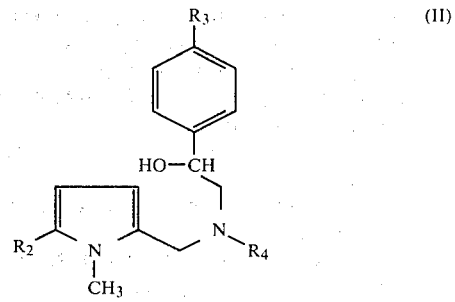

(II)

wherein
 $R_2$, $R_3$ and $R_4$ have the same meanings as in formula I.

The cyclization is effected with an acid cyclization agent, such as phosphoric or polyphosphoric acid, concentrated sulfuric acid or trifluoroacetic acid, without a solvent or in the presence of one or more inert solvents, such as methylene chloride, chloroform, dioxane, ethylene dichloride, benzene, toluene, xylene or chlorinated benzenes, at temperatures between room temperature and the reflux temperature of the particular solvent or mixture of solvents.
Method B
 For the preparation of a compound of the formula I wherein $R_2$ is —CH$_2$—A, by reacting a compound of the formula I wherein $R_2$ is hydrogen with formalin or paraformaldehyde and the corresponding amine. For this purpose a compound of the formula I wherein $R_2$ is hydrogen is dissolved in an inert, preferably water-miscible solvent, such as a lower alkanol or ethyl acetate, and adding to the solution the amine and the formalin or paraformaldehyde while heating. The resulting mixture is then heated, preferably under reflux, until the reaction has gone to completion and is subsequently worked up in conventional manner.
Method C
 For the preparation of a compound of the formula I wherein $R_2$ is chlorine or bromine, by chlorinating or brominating a compound of the formula I wherein $R_2$ is hydrogen. For bromination a compound of the formula I wherein $R_2$ is hydrogen, preferably in the form of an acid addition salt, is reacted in the cold or at room temperature with elemental bromine in an organic acid, such as acetic acid, or in an inert organic solvent, such as chlorinated hydrocarbons like carbon tetrachloride, methylene chloride or chloroform. The chlorination is advantageously carried out with an excess of sulfuryl chloride while slightly heating.
Method D
 For the preparation of a compound of the formula I wherein $R_4$ is alkyl, by reacting a compound of the formula I wherein $R_4$ is hydrogen with dialkyl sulfate or alkyl halide.

The compounds embraced by formula I are basic and therefore form addition salts with inorganic or organic acids. Examples of non-toxic, pharmacologically acceptable acid addition salts are those formed with a hydrohalic acid, sulfuric acid, phosphoric acid, aminosulfonic acid, formic acid, acetic acid, propionic acid, lactic acid, glycolic acid, gluconic acid, maleic acid, succinic acid, tartaric acid, benzoic acid, salicylic acid, citric acid, ascorbic acid, p-toluenesulfonic acid or oxyethanesulfonic acid.

Using the above-described methods of preparation, the following compounds of the formula I and their nontoxic, pharmacologically acceptable acid addition salts may, for example, be obtained:

1,6-dimethyl-4-phenyl-4,5,6,7-tetrahydro-pyrrolo[2,3-c]-pyridine;
1-methyl-4-(p-tolyl)-4,5,6,7-tetrahydro-pyrrolo[2,3-c]-pyridine;
1,6-dimethyl-4-(p-bromophenyl)-4,5,6,7-tetrahydropyrrolo-[2,3-c]-pyridine;
1,6-dimethyl-4-(p-methoxyphenyl)-4,5,6,7-tetrahydro-pyrrolo-[2,3-c]-pyridine;
1,6-dimethyl-4-(p-tolyl)-4,5,6,7-tetrahydropyrrolo-[2,3-c]-pyridine;
1-methyl-4-(p-tolyl)-6-ethyl-4,5,6,7-tetrahydropyrrolo-[2,3-c]-pyridine;
1,6-dimethyl-4-(p-chlorophenyl)-4,5,6,7-tetrahydropyrrolo-[2,3-c]-pyridine;
1,6-dimethyl-4-(p-fluorophenyl)-4,5,6,7-tetrahydropyrrolo-[2,3-c]pyridine;
2,6-dimethyl-4-(p-bromophenyl)-4,5,6,7-tetrahydropyrrolo-[2,3-c]pyridine;
1,6-dimethyl-2-hydroxymethyl-4-(p-chlorophenyl)-4,5,6,7-tetrahydro-pyrrolo[2,3-c]pyridine;
1,6-dimethyl-2-t-butyl-4-(p-chlorophenyl)-4,5,6,7-tetrahydro-pyrrolo[2,3-c]pyridine;
1,6-dimethyl-2-dimethylaminomethyl-4-(p-bromophenyl)-4,5,6,7-tetrahydro-pyrrolo[2,3-c]pyridine;
1,6-dimethyl-2-diethylaminomethyl-4-(p-bromophenyl)-4,5,6,7-tetrahydro-pyrrolo[2,3-c]pyridine;
1,6-dimethyl-2-pyrrolidinomethyl-4-(p-bromophenyl)-4,5,6,7-tetrahydro-pyrrolo[2,3-c]pyridine;
1,6-dimethyl-2-piperidinomethyl-4-(p-bromophenyl)-4,5,6,7-tetrahydro-pyrrolo[2,3-c]pyridine;
1,6-dimethyl-2-morpholinomethyl-4-(p-bromophenyl)-4,5,6,7-tetrahydro-pyrrolo[2,3-c]pyridine; and
1,6-dimethyl-2-N-methylpiperazinomethyl-4-(p-bromophenyl)-4,5,6,7-tetrahydro-pyrrolo[2,3-c]pyridine.

The starting compounds of the formula II may be obtained, for example, by reacting a correspondingly substituted N-methyl-pyrrole with formalin and phenylethanolamine under the conditions of the Mannich reaction [cf. Angewandte Chemie 68, 265, (1956)].

The following examples illustrate the present invention and will enable others skilled in the art to understand it more completely. It should be understood, however, that the invention is not limited solely to the particular examples given below.

EXAMPLE 1

1,6-Dimethyl-4-phenyl-4,5,6,7-tetrahydro-pyrrolo[2,3-c]-pyridine and its maleate 12 gm (0.049 mol) of N-methyl-N-(1-methylpyrrolyl[2]-methyl)-2-hydroxy-2-phenyl-ethylamine were added to 150 gm of polyphosphoric acid, and the mixture was stirred for one hour at 40°–45° C. Subsequently, it was diluted with 1 liter of ice water and made alkaline with concentrated ammonia. The reaction mixture was extracted several times with ethyl acetate, the ethyl acetate extracts were evaporated, and the residue was chromatographed on 200 gm of silicagel (ethyl acetate: cyclohexane=3:1). The title compound was precipitated as its maleate.
Yield: 10.5 gm (63% of theory);
M.p.: 177°–178° C. (from ethanol).

EXAMPLE 2

1-Methyl-4-(p-tolyl)-4,5,6,7-tetrahydro-pyrrolo[2,3-c]-pyridine and its maleate

To 70 ml of methane sulfonic acid heated to 40° C., a solution of 10 gm (0.04 mol) of N-(1-methylpyrrolyl-[2]-methyl)-2-(p-tolyl)-2-hydroxy-ethylamine in 70 ml of ethylene chloride was added dropwise in such a way that the temperature did not exceed 50° C. The reaction mixture was kept at this temperature for 45 minutes. Subsequently, it was admixed with 500 gm of ice, made alkaline with ammonia, extracted with methylene chloride, and after evaporation of the solvent, the title compound was precipitated as its maleate.
Yield: 8 gm (57% of theory);
M.p.: 162°–163° C. (from ethanol).

EXAMPLE 3

1,6-Dimethyl-2-morpholinomethyl-4-phenyl-4,5,6,7-tetrahydropyrrolo[2,3-c]pyridine A mixture of 1.7 gm of 1,6-dimethyl-4-phenyl-4,5,6,7-tetrahydro-pyrrolo[2,3-c]pyridine maleate, 5 ml of glacial acetic acid, 2 ml of a 30% formalin solution and 1.5 ml of morpholine was stirred for 15 minutes at room temperature. Afterwards, the resulting solution was made alkaline with concentrated ammonia and extracted twice with ether. The organic phase was washed twice with water and, after drying, evaporated in vacuo. The residue crystallized from diisopropylether. 700 mg=43.3% of theory of the title compound were obtained;
M.p.: 96°–97° C.

EXAMPLE 4

1,6-Dimethyl-4-(p-bromophenyl)-4,5,6,7-tetrahydropyrrolo[2,3-c]pyridine and its maleate (a) N-Methyl-N-(1-methylpyrrolyl-[2]-methyl)-2-(p-bromophenyl)-2-hydroxy-ethylamine 62 gm (0.5 mol) of N-(1-methylpyrrolyl-[2]-methyl-N-methylamine and 199 gm (0.5 mol) of p-bromostyroloxide were admixed and heated to 90° C. During the ensuing exothermic reaction, the temperature was kept at 100° to 110° C. by cooling. Then, the reaction mixture was heated at 100° C. for another half hour. After cooling, the title compound crystallized from cyclohexane.
Yield: 110 gm (68% of theory);
M.p.: 78°–79° C. (from cyclohexane).

(b) 20 gm (0.62 mol) of N-methyl-N-(1-methylpyrrolyl[2]-methyl)-2-(p-bromophenyl)-2-hydroxy-ethylamine were cyclized in 200 gm of polyphosphoric acid, analogous to Example 1, and the reaction mixture was worked up. 11 gm (58% of theory) of the free base were obtained; M.p.: 77°–78° C. (from cyclohexane/petroleum ether). The base was converted in conventional manner into its maleate, m.p. 175°–176° C.

Using procedures analogous to those described above, the following compounds of the formula I were also prepared:

TABLE I

| Example No. | $R_2$ | $R_3$ | $R_4$ | M.p. °C. |
|---|---|---|---|---|
| 5 | —H | —Br | —H | 166–167 MA |
| 6 | —H | —CH$_3$ | —CH$_3$ | 212–215 CL |

TABLE I-continued

| Example No. | R₂ | R₃ | R₄ | M.p. °C. |
|---|---|---|---|---|
| 7 | —H | —CH₃ | —C₂H₅ | 255-257 CL |
| 8 | —H | —Cl | —CH₃ | 226-227 CL |
| 9 | —H | —F | —CH₃ | 240-241 CL |
| 10 | —CH₂—N(piperidine) | —Br | —CH₃ | 161-162 MA |
| 11 | —C(CH₃)₃ | —Cl | —CH₃ | 265-267 CL |
| 12 | —NO₂ | —Br | —CH₃ | 177-178 |
| 13 | —Br | —Br | —CH₃ | 88-89 |
| 14 | —Cl | —Br | —CH₃ | 213-214 CL |
| 15 | —CH₃ | —Br | —CH₃ | 173-174 MA |
| 16 | —CN | —Br | —CH₃ | 145-146 |
| 17 | CH₃—C(=O)— | —Br | —CH₃ | 262-264 CL |
| 18 | H—C(=O)— | —F | —CH₃ | 272-274 CL |
| 19 | (CH₃)₂N—CH₂— | —Br | —CH₃ | 164-165 MA₂ |
| 20 | (pyrrolidine)N—CH₂— | —Br | —CH₃ | 169-170 MA₂ |
| 21 | (hexahydroazepine)N—CH₂— | —Br | —CH₃ | 154-155 MA₂ |
| 22 | (piperidine)N—CH₂— | —CH₃ | —C₂H₅ | 150-151 MA₂ |
| 23 | (morpholine)N—CH₂— | —Br | —CH₃ | 248-249 MA₂ |
| 24 | (piperidine)N—CH₂— | —CH₃ | —CH₃ | 163-164 MA₂ |
| 25 | (hexahydroazepine)N—CH₂— | —CH₃ | —CH₃ | 161-162 MA₂ |
| 26 | HO—CH₂—CH₂—N(CH₃)—CH₂— | —Br | —CH₃ | 132-133 MA₂ |
| 27 | HO-(piperidine)-N—CH₂— | —Br | —CH₃ | 152-153 MA₂ |
| 28 | HO—CH₂-(pyrrolidine)-N—CH₂— | —Br | —CH₃ | 112-114 MA₂ |
| 29 | HO-(piperidine)-N—CH₂— | —Br | —CH₃ | 249-250 MA₂ |
| 30 | HO—CH₂—CH₂—N(CH₂CH₃)—CH₂— | —F | —CH₃ | 104-106 MA₂ |
| 31 | HO—CH₂—CH₂—N(CH₃)—CH₂— | —CH₃ | —CH₃ | 120-121 MA₂ |

MA = maleate
CL = hydrochloride
MA₂ = dimaleate

The compounds of the present invention, that is, those embraced by formula I above and their non-toxic, pharmacologically acceptable acid addition salts, have useful pharmacodynamic properties. More particularly, they exhibit antidepressant activity in warm-blooded animals such as mice, which manifests itself as a thymoleptic (mood-elevating) and central stimulating effect.

It is now believed that various forms of depression cause a deficiency of certain physiologically important amines, particularly noradrenaline and serotonin, in certain parts of the brain, and that the amount of such amines may be increased by inhibiting their uptake by neurons. In a suitable test arrangement, we have shown that the novel compounds not only inhibit the uptake of serotonin, but also that of noradrenaline by the neurons, thus indicating that they are superior to known commercial products, for example nomifensin, as the latter generally only inhibit the uptake of noradrenaline.

The test is performed on the homogenized, isolated cerebrum of the rat. A suspension of synaptosomes thus obtained is incubated with deuterium-labeled noradrenaline and/or serotonin and various concentrations of a solution of the test substance in water for 10 minutes at 37° C. When the incubation is finished, the medium is separated by filtering, and the radioactivity of the suspension of synaptosomes is measured.

A control test in the absence of the test substance is simultaneously carried out in order to determine the quantity of radioactive amines taken up. The quantity of the test substance in mols which is required to inhibit 50% of the uptake is designated the IC 50.

A further test for determining anti-depressive activity is based on reserpine-antagonism, that is, the elimination of the hypothermic effect caused by reserpine. The test is carried out in mice, 5 animals being used per dosage test. Seventeen hours after i.p. administration of 2 mg/kg of reserpine, the body temperature is measured peripherally while at a room temperature of 19° C. Afterwards, the test substance is administered orally, and the body temperature is measured after 1, 3, 5 and 7 hours. For each measured period a mean effective dose (ED₅₀) is determined. This is the dosage at which the body temperature of the animals treated with reserpine approaches the normal temperature of untreated controls by 50%.

The following table shows the results of these tests for a few representative species of the genus:

TABLE II

| Compound | Reserpine antagonism after hours (mg/kg) | | | | Serotonin inhibition IC 50 (Mol) | Noradrenaline inhibition IC 50 (Mol) |
|---|---|---|---|---|---|---|
| | 1 | 3 | 5 | 7 | | |
| 1,6-dimethyl-4-(p-bromophenyl)-4,5,6,7-tetrahydro-pyrrolo- | 20 | 6 | 40 | 40 | $0.9 \cdot 10^{-7}$ | $1.25 \cdot 10^{-6}$ |

TABLE II-continued

| Compound | Reserpine antagonism after | | | | Serotonin inhibition IC 50 (Mol) | Noradrenaline inhibition IC 50 (Mol) |
| --- | --- | --- | --- | --- | --- | --- |
| | 1 | 3 | 5 | 7 | | |
| | hours (mg/kg) | | | | | |
| [2,3-c]pyridine maleate | | | | | | |
| 1-methyl-4-(p-bromophenyl)-4,5,6,7-tetrahydro-pyrrolo-[2,3-c]pyridine maleate | 36 | 10 | 30 | 40 | $0.53 \cdot 10^{-6}$ | $6.9 \cdot 10^{-6}$ |
| 1,6-dimethyl-4-(p-tolyl)-4,5,6,7-tetrahydro-pyrrolo-[2,3-c]pyridine hydrochloride | >40 | <10 | 16 | <10 | $0.4 \cdot 10^{-7}$ | $4.9 \cdot 10^{-6}$ |
| 1-methyl-4-(p-tolyl)-6-ethyl-4,5,6,7-tetrahydro-pyrrolo-[2,3-c]pyridine hydrochloride | >40 | <10 | 10 | >40 | $0.2 \cdot 10^{-7}$ | $0.6 \cdot 10^{-6}$ |
| 1,6-dimethyl-4-(p-chlorophenyl)-4,5,6,7-tetrahydro-pyrrolo-[2,3-c]pyridine hydrochloride | <10 | <10 | <10 | <10 | $0.4 \cdot 10^{-7}$ | $1.5 \cdot 10^{-6}$ |
| 1,6-dimethyl-4-(p-fluorophenyl)-4,5,6,7-tetrahydro-pyrrolo-[2,3-c]pyridine hydrochloride | <10 | <10 | <10 | <10 | $0.18 \cdot 10^{-6}$ | $6.7 \cdot 10^{-6}$ |
| 1,6-dimethyl-2-morpholino-methyl-4-phenyl-4,5,6,7-tetrahydro-pyrrolo[2,3-c]-pyridine | >40 | 16 | 10 | <40 | $1.6 \cdot 10^{-6}$ | $6.6 \cdot 10^{-6}$ |
| 1,6-dimethyl-2-piperidino-methyl-4-(p-bromophenyl)-4,5,6,7-tetrahydro-pyrrolo-[2,3-c]pyridine dimaleate | >40 | 40 | 40 | >40 | $1.0 \cdot 10^{-6}$ | $2.15 \cdot 10^{-6}$ |
| 1,6-dimethyl-2-pyrrolidino-methyl-4-(p-bromophenyl)-4,5,6,7-tetrahydro-pyrrolo-[2,3-c]pyridine dimaleate | >40 | <10 | 10 | <10 | $0.76 \cdot 10^{-6}$ | $2.1 \cdot 10^{-6}$ |
| 1,6-dimethyl-2-N-methyl-N-β-hydroxyethyl-aminomethyl-4-(p-bromophenyl)-4,5,6,7-tetrahydro-pyrrolo[2,3-c]-pyridine dimaleate | 10 | <10 | 13 | 10 | $0.38 \cdot 10^{-6}$ | $1.3 \cdot 10^{-6}$ |
| 1,6-dimethyl-2-hexahydro-azepine-1-yl-methyl-4-(p-bromophenyl)-4,5,6,7-tetrahydro-pyrrolo[2,3-c]-pyridine dimaleate | <10 | <10 | 20 | >40 | $0.94 \cdot 10^{-6}$ | $1.5 \cdot 10^{-6}$ |
| 1,6-dimethyl-2-bromo-4-(p-bromophenyl)-4,5,6,7-tetrahydro-pyrrolo[2,3-c]-pyridine | >40 | 14 | <10 | 10 | $0.44 \cdot 10^{-6}$ | $1.8 \cdot 10^{-6}$ |

For pharmaceutical purposes the compounds of the present invention are administered to warm-blooded animals perorally, parenterally or rectally as active ingredients in customary dosage unit compositions, that is, compositions in dosage unit form consisting essentially of an inert pharmaceutical carrier and one effective dosage unit of the active ingredient, such as tablets, coated tablets, capsules, wafers, powders, solutions, suspensions, emulsions, syrups, suppositories and the like. One effective dosage unit of the compound according to the present invention is from 0,0166 to 1,25 mgm/kg body weight, preferably 0,3 mgm/kg body weight.

The following examples illustrate a few pharmaceutical dosage unit compositions comprising a compound of the present invention as an active ingredient and represent the best modes contemplated of carrying out the invention. The parts are part by weight unless otherwise specified.

EXAMPLE 32

Coated tablets

The tablet core composition is compounded from the following ingredients:

| | |
| --- | --- |
| 1,6-Dimethyl-4-phenyl-4,5,6,7-tetrahydro-pyrrolo[2,3-c] | |
| pyridine | 25.0 parts |
| Lactose | 50.0 parts |
| Corn starch | 22.0 parts |
| Gelatin | 2.0 parts |
| Magnesium stearate | 1.0 parts |
| Total | 100.0 parts |

Preparation:

The active ingredient, the lactose and the corn starch are intimately admixed with each other, the mixture is moistened with an aqueous 10% solution of the gelatin, the moist mass is granulated through a 1 mm-mesh screen, and the granulate is dried at 40° C. and again passed through the screen. The dry granulate is admixed with the magnesium stearate, and the composition is compressed into 100 mgm-tablet cores which are subsequently coated with a thin shell consisting essentially of a mixture of sugar, titanium dioxide, talcum and gum arabic, and polished with beeswax. Each coated tablet is an oral dosage unit composition containing 25 mgm of the active ingredient.

EXAMPLE 33

Tablets

The tablet composition is compounded from the following ingredients:

| | |
|---|---|
| 1,6-Dimethyl-4-phenyl-4,5,6,7-tetrahydro-pyrrolo[2,3-c] pyridine | 10.0 parts |
| Lactose | 40.0 parts |
| Corn starch | 44.0 parts |
| Soluble starch | 5.0 parts |
| Magnesium stearate | 1.0 parts |
| Total | 100.0 parts |

Preparation:

The active ingredient and the magnesium stearate are intimately admixed with each other, the mixture is moistened with an aqueous solution of the soluble starch, the moist mass is granulated, the granulate is dried, and the dry granulate is thoroughly admixed with the lactose and the corn starch. The composition is compressed into 100 mgm-tablets, each of which is an oral dosage unit composition containing 10 mgm of the active ingredient.

EXAMPLE 34

Suppositories

The suppository composition is compounded from the following ingredients:

| | |
|---|---|
| 1,6-Dimethyl-4-phenyl-4,5,6,7-tetrahydro-pyrrolo[2,3-c] pyridine | 10.0 parts |
| Suppository base (e.g. cocoa butter) | 1,690.0 parts |
| Total | 1,700.0 parts |

Preparation:

The finely pulverized active ingredient is homogeneously blended into the suppository base which had previously been melted and cooled to 40° C. The composition is cooled to 35° C., and 1700 mgm-portions thereof are poured into cooled suppository molds and allowed to harden therein. Each suppository is a rectal dosage unit composition containing 10 mgm of the active ingredient.

EXAMPLE 35

Hypodermic solution

The solution is compounded from the following ingredients:

| | |
|---|---|
| 1,6-Dimethyl-4-phenyl-4,5,6,7-tetrahydro-pyrrolo[2,3-c]-pyridine maleate | 5.0 parts |
| Sodium pyrosulfite | 1.0 parts |
| EDTA disodium salt | 0.5 parts |
| Sodium chloride | 8.5 parts |
| Double distilled water q.s. ad | 1000.0 parts |

Preparation:

The active ingredient and the excipients are dissolved in a sufficient ammount of double-distilled water, and the solution is diluted with the remaining amount of double-distilled water. The solution is then filtered until free from suspended particles, and the filtrate is filled under aseptic conditions into 1 cc-ampules which are subsequently sterilized and sealed. The contents of each ampule are an injectable dosage unit composition containing 5 mgm of the active ingredient.

Any one of the other compounds embraced by formula I or a non-toxic, pharmacologically acceptable acid addition salt thereof may be substituted for the particular active ingredient in Examples 32 through 35. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

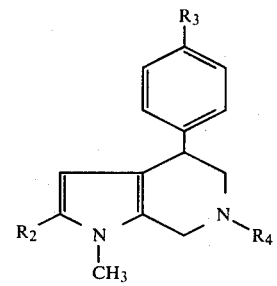

wherein

R$_2$ is hydrogen, chlorine, bromine, formyl, acetyl, alkyl of 1 to 4 carbon atoms, nitro, cyano or —CH$_2$—A;

where

A is (alkyl of 1 to 2 carbon atoms)-amino; di(alkyl of 1 to 2 carbon atoms)-amino, where one of the alkyl moieties may have at terminal hydroxyl substituent attached thereto; or a 5-, 6- or 7-membered saturated heterocycle containing a single ring nitrogen atom, which is attached to the methylene group through the nitrogen atom and may have a hydroxyl or hydroxymethyl substituent attached to a ring carbon atom, and the 6-membered heterocycle may contain oxygen as an additional ring heteroatom in the p-position;

R$_3$ is hydrogen, fluorine, chlorine, bromine, methyl or methoxy; and

R$_4$ is hydrogen or alkyl of 1 to 3 carbon atoms;

or a non-toxic, pharmacologically acceptable acid addition salt thereof.

2. A compound of claim 1, where

R$_2$ is hydrogen, chlorine, bromine, fluorine, formyl, acetyl, methyl, nitro, cyano or —CH$_2$—A, where A is dimethylamino, N-(β-hydroxyethyl)-methylamino, N-(β-hydroxyethyl)-ethylamino, morpholino, piperidino, hydroxy-piperidino, hydroxymethyl-piperidino, hexamethyleneimino or pyrrolidino;

R$_3$ is hydrogen, fluorine, chlorine, bromine or methyl; and

R$_4$ is hydrogen, methyl or ethyl;

or a non-toxic, pharmacologically acceptable acid addition salt thereof.

3. A compound of claim 2, which is 1,6-dimethyl-2-(pyrrolidino-methyl)-4-(p-bromo-phenyl)-4,5,6,7-tetrahydro-pyrrolo[2,3-c]pyridine or a non-toxic, pharmacologically acceptable acid addition salt thereof.

4. A compound of claim 2, which is 1,6-dimethyl-4-(p-bromo-phenyl)-4,5,6,7-tetrahydropyrrolo[2,3-c]pyridine or a non-toxic, pharmacologically acceptable acid addition salt thereof.

5. A compound of claim 2, which is 1-methyl-4-(p-bromo-phenyl)-4,5,6,7-tetrahydro-pyrrolo[2,3-c]pyridine or a non-toxic, pharmacologically acceptable acid addition salt thereof.

6. A compound of claim 2, which is 1,6-dimethyl-2-(piperidino-methyl)-4-(p-bromo-phenyl)-4,5,6,7-tetrahydro-pyrrolo[2,3-c]pyridine or a non-toxic, pharmacologically acceptable acid addition salt thereof.

7. A compound of claim 2, which is 1,6-dimethyl-2-bromo-4-(p-bromo-phenyl)-4,5,6,7-tetrahydropyrrolo[2,3-c]pyridine or a non-toxic, pharmacologically acceptable acid addition salt thereof.

8. A compound of claim 2, which is 1,6-dimethyl-2-(N-methyl-N-ω-hydroxyethyl-amino-methyl)-4-(p-bromo-phenyl)-4,5,6,7-tetrahydro-pyrrolo[2,3-c]pyridine or a non-toxic, pharmacologically acceptable acid addition salt thereof.

9. An antidepressant pharmaceutical dosage unit composition consisting essentially of an inert pharmaceutical carrier and an effective antidepressant amount of a compound of claim 1.

10. The method of stimulating the mood of a depressed warm-blooded animal, which comprises administering to said animal an effective antidepressant amount of a compound of claim 1.

* * * * *